United States Patent
McCroskey et al.

(10) Patent No.: US 8,946,643 B2
(45) Date of Patent: Feb. 3, 2015

(54) VIRTUAL PIXELATED DETECTOR FOR PET AND/OR SPECT

(75) Inventors: William K. McCroskey, Solon, OH (US); Timothy W. Milliff, Montville, OH (US); William D. Dickinson, Northfield, OH (US)

(73) Assignee: FMI Technologies, Inc., Akron, OH (US)

( * ) Notice: Subject to any disclaimer, the term of this patent is extended or adjusted under 35 U.S.C. 154(b) by 729 days.

(21) Appl. No.: 13/269,601

(22) Filed: Oct. 9, 2011

(65) Prior Publication Data

US 2012/0085913 A1   Apr. 12, 2012

Related U.S. Application Data

(60) Provisional application No. 61/391,619, filed on Oct. 9, 2010.

(51) Int. Cl.
 G01T 1/202 (2006.01)
(52) U.S. Cl.
 CPC ..................................... G01T 1/202 (2013.01)
 USPC ....................................................... 250/366
(58) Field of Classification Search
 CPC ...................................................... G01T 1/202
 USPC .................................. 250/363.01, 363.04, 366
 See application file for complete search history.

(56) References Cited

U.S. PATENT DOCUMENTS

| | | | |
|---|---|---|---|
| 6,362,479 B1 | 3/2002 | Andreaco et al. | |
| 7,238,943 B2 * | 7/2007 | Wong et al. | 250/367 |
| 7,304,309 B2 | 12/2007 | Suhami | |
| 7,635,848 B2 | 12/2009 | Nelson | |
| 7,723,694 B2 | 5/2010 | Frach et al. | |
| 8,063,377 B2 * | 11/2011 | Schulz | 250/366 |
| 2003/0128801 A1 * | 7/2003 | Eisenberg et al. | 378/19 |
| 2007/0131858 A1 | 6/2007 | Wollenweber et al. | |
| 2009/0065700 A1 * | 3/2009 | Menge et al. | 250/368 |
| 2009/0314947 A1 | 12/2009 | Goushcha et al. | |
| 2009/0324042 A1 | 12/2009 | Laurence et al. | |
| 2010/0044571 A1 * | 2/2010 | Miyaoka et al. | 250/362 |
| 2010/0172565 A1 | 7/2010 | Degenhardt et al. | |
| 2010/0219345 A1 * | 9/2010 | Franch et al. | 250/362 |
| 2010/0219347 A1 | 9/2010 | Schulz et al. | |

FOREIGN PATENT DOCUMENTS

| | | | |
|---|---|---|---|
| WO | 2006111883 | 10/2006 | |
| WO | 2009019659 | 2/2009 | |
| WO | WO 2009024895 A3 * | 4/2009 | G01T 1/20 |

* cited by examiner

*Primary Examiner* — David Porta
*Assistant Examiner* — Faye Boosalis
(74) *Attorney, Agent, or Firm* — Dominic A. Frisina

(57) ABSTRACT

A slab detector for PET and/or SPECT imaging comprising a scintillation crystal slab and a plurality of photoconverters each in optical communication with a surface of the scintillation crystal. In some embodiments, the plurality of photoconverters define a two dimensional array, wherein each photoconverter abuts adjacent photoconverters. Furthermore, according to some embodiments a plurality of slab detectors can be juxtaposed with one another so that their slab crystals abut edgewise.

19 Claims, 5 Drawing Sheets

VIRTUAL PIXELATED DETECTOR FOR PET AND/OR SPECT

I. CROSS-REFERENCE TO RELATED APPLICATIONS

The present application claims priority to U.S. Provisional Application No. 61/391,619, filed Oct. 9, 2010, and which is incorporated by reference in its entirety.

II. BACKGROUND OF THE INVENTION

A. Field of Invention

This invention generally relates to detectors for positron emission tomography (PET), and/or single photon emission computed tomography (SPECT).

B. Description of the Related Art

PET and SPECT imaging devices operate by sensing gamma radiation emitted by radiopharmaceuticals that have accumulated in target organs or tissues of a patient. A two or three dimensional image is constructed by mapping the positions of particular gamma sources. With specific reference to a PET experiment, a selected radiopharmaceutical is administered to a patient, which can comprise any of a wide variety of physiologically relevant molecules. The suitability of a radiopharmaceutical depends, in part, upon the organ or tissue to be imaged. One particularly common choice is fluorodeoxyglucose (FDG), which is a molecule of glucose where a hydroxyl group is substituted with $^{18}F$. $^{18}F$ is a $\beta^+$ emitter meaning that it undergoes the following nuclear decay reaction:

$$^{18}F \rightarrow {}^{18}O + \beta^+ + \nu + e-$$ eq. 1 where $\beta^+$ is a positron, v is a neutrino, and e– is an electron. The positron is ejected from the nucleus of $^{18}F$ with substantial kinetic energy, which must be almost entirely dissipated before the positron can combine with an electron in an annihilation event. In general, dissipative processes can be elastic or inelastic scattering with any surrounding matter in the path of the positron, including electrons and nuclei. Statistically, positrons travel about 1 mm before losing enough kinetic energy to combine with an electron and annihilate. When annihilation occurs, a pair of 511 keV gamma photons is created equaling the energy equivalent of the annihilated particles, and radiating at close to 180° from each other. In the ideal case where the positron and electron both have zero momentum at the time of annihilation, the gamma photons would emit at exactly 180°. Deviation from 180° by about +/–0.5° indicates that the annihilation event occurred with particles having residual momentum.

It is known to place a pair of PET detectors 180° from each other to detect a pair of gamma photons emitted from a single annihilation event, and calculate the position of the annihilation event from the data collected. In some cases, the two or more PET detectors are rotated around the patient, and in others PET detectors form a continuous ring about the patient, thus requiring no rotation. In either case, the respective detectors collect gamma photons and either accept or reject the data depending in part on whether the photon was within an acceptable range about 511 keV, and whether it arrived within an acceptable time window to correlate one gamma photon to another. When a match is found between gamma photons, i.e. they are determined to have originated from the same annihilation event, a line of response (LOR) can be drawn between the two points on the respective detectors where the photons were detected. Accordingly, the position of the annihilation event must be located somewhere along the LOR. Some instruments are capable of sufficient temporal resolution to calculate the position of the annihilation event based on the difference in the time of flight (TOF) of the pair of gamma photons. In lower resolution instruments other mathematical methods must be used to calculate annihilation position based on interpolation and/or extrapolation algorithms.

Traditionally PET/SPECT detectors include a plurality of scintillation crystals arranged in a pixelated two-dimensional array and spaced apart with septum material, which limits optical interference between adjacent crystals. The array of scintillation crystals is placed in optical communication with a plurality of photoconverters also arranged in a two-dimensional array. Often, one photoconverter will be in optical communication with a plurality of scintillation crystals. When a scintillation crystal receives a gamma photon, the photon travels some finite distance within the crystal before finally being absorbed. This distance, is known as the depth of interaction (DOI). At the position where the gamma photon is absorbed, the crystal emits a large number of UV and/or visible photons, i.e. it scintillates. The photon wave front propagates within the crystal and contacts the photoconverters. Traditionally, the photoconverters continuously integrate the photonic signal and are read individually based on whether they reach a minimum threshold signal intensity, and the data may be digitized thereafter. A center-of-mass calculation is then used to estimate the position of the scintillation event. From this data, parameters can be calculated for image reconstruction. For example, known image reconstruction algorithms can then be applied to the data to create an image. Such image reconstruction algorithms can include Filtered Back Projection and/or Ordered Subset Expectation Maximization. The reconstructed image can then be displayed according to known image display algorithms such as maximum intensity projection (MIP) and/or minimum intensity projection (mIP).

What is needed is an unpixelated slab detector, which would enable more precise calculations of, for example, depth of interaction and/or other parameters necessary to reconstruct high resolution images. Some embodiments of the present invention overcome one or more limitations of the prior art.

III. SUMMARY OF THE INVENTION

Some embodiments relate to a slab detector, comprising: a scintillation crystal slab having a first major surface for receiving gamma rays, the first major surface including a reflective coating suitable for reflecting scintillation photons, a second major surface being free from reflective coatings and spaced apart from the first major surface defining a thickness, wherein the first and second major surfaces are each bounded by four edges which collectively define four minor surfaces, each minor surface including a reflective coating suitable for reflecting scintillation photons; and a plurality of photoconverters each in optical communication with the second major surface of the scintillation crystal and defining a two dimensional array, wherein each photoconverter abuts adjacent photoconverters.

According to some embodiments the scintillation crystal slab comprises a single crystal.

According to some embodiments the scintillation crystal slab comprises a plurality of crystals joined by an index-matching material.

According to some embodiments the scintillation crystal slab is free from pixelation grooves.

According to some embodiments the scintillation crystal slab further comprises one or more pixelation grooves.

According to some embodiments one of the first or second major surfaces is curved, defining a lens.

According to some embodiments the lens is adapted to focus scintillation photons on a predetermined portion of the two-dimensional array of photoconverters, or the lens is adapted to collimate scintillation photons such that they impinge the two-dimensional array of photoconverters at a perpendicular angle relative to the two-dimensional array.

According to some embodiments the scintillation crystal comprises a material selected from one or more of cerium doped lutetium yttrium orthosilicate, sodium doped cesium iodide, bismuth germinate, cerium doped gadolinium orthosilicate, thallium doped sodium iodide, barium fluoride, cerium doped yttrium aluminate, cerium doped lutetium oxyorthosilicate, lanthanum bromide, cerium doped lanthanum bromide, or any combination thereof.

According to some embodiments the plurality of photoconverters is selected from one or more of a silicon photomultiplier, or an avalanche photodiode.

Some embodiments further comprise a data processing module in electronic communication with each of the photoconverters, and adapted to collect data from each photoconverter simultaneously and in a manner suitable for decimation in time sampling of a photon wave front in real time.

According to some embodiments a plurality of detectors according to claim 1 are adapted to be juxtaposed with each other such that the scintillation crystal slabs of the respective detectors abut edgewise.

Some embodiments relate to a slab detector, comprising: a scintillation crystal slab having a first major surface for receiving gamma rays, the first major surface including a reflective coating suitable for reflecting scintillation photons, a second major surface including a reflective coating suitable for reflecting scintillation photons and spaced apart from the first major surface defining a thickness, wherein the first and second major surfaces are each bounded by four edges which collectively define four minor surfaces, each minor surface being free from reflective coatings; and a plurality of photoconverters in optical communication with a minor surface of the scintillation crystal slab, and wherein each minor surface is in optical communication with at least one photoconverter.

According to some embodiments the scintillation crystal slab comprises a single crystal.

According to some embodiments the scintillation crystal slab comprises a plurality of crystals joined by an index-matching material.

According to some embodiments one or more surfaces is curved, defining a lens.

According to some embodiments the lens is adapted to focus scintillation photons on a predetermined portion of the plurality of photoconverters, or the lens is adapted to collimate scintillation photons such that they impinge the plurality of photoconverters at a perpendicular angle relative to the two-dimensional array.

According to some embodiments the scintillation crystal comprises a material selected from one or more of cerium doped lutetium yttrium orthosilicate, sodium doped cesium iodide, bismuth germinate, cerium doped gadolinium orthosilicate, thallium doped sodium iodide, barium fluoride, cerium doped yttrium aluminate, cerium doped lutetium oxyorthosilicate, lanthanum bromide, cerium doped lanthanum bromide, or any combination thereof.

According to some embodiments the plurality of photoconverters is selected from one or more of a silicon photomultiplier, or an avalanche photodiode.

Some embodiments further comprise a data processing module in electronic communication with each of the photoconverters, and adapted to collect data from each photoconverter simultaneously and in a manner suitable for decimation in time sampling of a photon wave front in real time.

Some embodiments relate to a slab detector, comprising: a scintillation crystal slab comprising a single crystal having a first major surface for receiving gamma rays, the first major surface including a reflective coating suitable for reflecting scintillation photons, a second major surface being free from reflective coatings and spaced apart from the first major surface defining a thickness, wherein the first and second major surfaces are each bounded by four edges which collectively define four minor surfaces, each minor surface including a reflective coating suitable for reflecting scintillation photons, and wherein one of the first or second major surfaces is curved, defining a lens; and a plurality of photoconverters each in optical communication with the second major surface of the scintillation crystal and defining a two dimensional array, wherein each photoconverter abuts adjacent photoconverters, wherein the lens is adapted to focus scintillation photons on a predetermined portion of the plurality of photoconverters, or the lens is adapted to collimate scintillation photons such that they impinge the two-dimensional array of photoconverters at a perpendicular angle relative to the two-dimensional array.

Other benefits and advantages will become apparent to those skilled in the art to which it pertains upon reading and understanding of the following detailed specification.

IV. BRIEF DESCRIPTION OF THE DRAWINGS

The invention may take physical form in certain parts and arrangement of parts, embodiments of which will be described in detail in this specification and illustrated in the accompanying drawings which form a part hereof and wherein.

V. DETAILED DESCRIPTION OF THE INVENTION

According to some embodiments, a PET/SPECT tomographic imaging system comprises at least a single continuous slab scintillation crystal having planar upper and lower faces. A face of the crystal is in optical communication with a plurality of high-speed photoconverters, which are adapted to synchronously detect scintillation events in the crystal. Suitable photoconverters can include, without limitation, a silicon photomultiplier (SiPM) array, or an array of avalanche photodiodes. Alternatively, in some embodiments the slab crystal can include one major surface having a curved 501 geometry and defining a lens. According to such embodiments, the crystal can comprise one or more of a focusing lens or a collimating lens.

Particularly, the plurality of photoconverters is adapted to synchronously obtain a time series of digital samples of a wave front in real time, the time series comprising a decimation in time sampling. According to some embodiments of the invention, one or more algorithms are applied to the digital pulse data, which can enhance temporal resolution up to about 4 picoseconds. Subsequently, one or more other algorithms are then applied to the resulting high temporal resolution data using a Pulse Wave Front digital processor to achieve high precision calculations of pulse energy, pulse time, scintillation event position, annihilation x-y position, gamma photon time-of-flight (TOF), and gamma photon depth-of-interaction (DOI) with the scintillation crystal. Some embodiments optionally include a continuous digital pulse pileup correction algorithm for deconvoluting multiple event signals occurring on a single-slab scintillation crystal.

According to some embodiments suitable scintillation crystals can comprise one or more of cerium doped lutetium yttrium orthosilicate (LYSO), sodium doped cesium iodide (Na:CsI), bismuth germinate (BGO), cerium doped gadolinium orthosilicate (GSO), thallium doped sodium iodide (Tl:NaI), barium fluoride ($BaF_2$), cerium doped yttrium aluminate ($YAlO_3$, i.e. YAP), cerium doped lutetium oxyorthosilicate ($Ce:Lu_2SiO_5$, i.e. LSO), lanthanum bromide ($LaBr_3$), cerium doped lanthanum bromide, or any combination thereof.

Some embodiments include scintillation crystals having a reflective coating, or a reflective member, on one or more surfaces of a scintillation crystal to prevent loss of scintillation photons. Furthermore, in some embodiments every surface, except that which is in optical communication with one or more photoconverters, includes a reflective coating or member. Numerous suitable transparent reflective coatings are known in the art. Typical reflective members can include polytetrafluoroethylene (PTFE) tape or any of a wide variety of diffuse reflector materials.

Figure 1A:
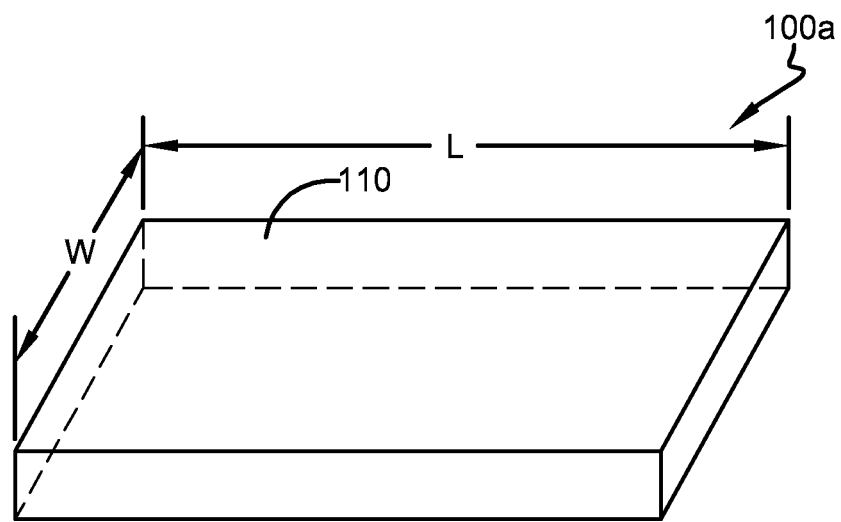
FIG. 1A is a perspective view of a slab scintillation crystal of an embodiment.

Suitable scintillation detectors can take a variety of forms. For example, in some embodiments a suitable detector can comprise a single slab of a scintillation crystal 100a as shown in FIG. 1A. In some embodiments, the slab can have no pixelation grooves, or it can include one or more pixelation grooves 120 disposed on one or more faces 110 of the crystal 100b. Furthermore, some scintillation crystals may not be available as a single crystal in large enough sizes for a slab detector. Thus, some embodiments 200 can comprise a plurality of scintillation crystals 201a, 201b, 201c, and 201d joined using an index-matching material 210 that matches the index of refraction of the crystals being joined 201a-d thereby limiting or eliminating interfacial reflections, i.e. Fresnel reflections. Suitable index-matching materials can include any of a variety of optical adhesives known in the art, which are characterized by indices of refraction similar to that of the scintillation crystal. One of skill in the art will recognize that the proper choice of index-matching material will depend on the specific scintillation crystal selected for use in the detector.

For example, according to some embodiments a scintillation detector can comprise a single slab of LYSO crystal 200b, while other embodiments 200a can comprise a plurality of smaller LYSO crystals 201a-d, wherein each is a rectangular subunit joined together using an index matching material 210. Thus, the plurality of joined LYSO crystals 200a can have similar overall dimensions to that of the single slab LYSO crystal 200b. Furthermore, in some embodiments each of the plurality of joined LYSO crystals 101a-d can comprise an area of about one quarter that of an overall area of the plurality of joined crystals 200a.

Figure 1B:
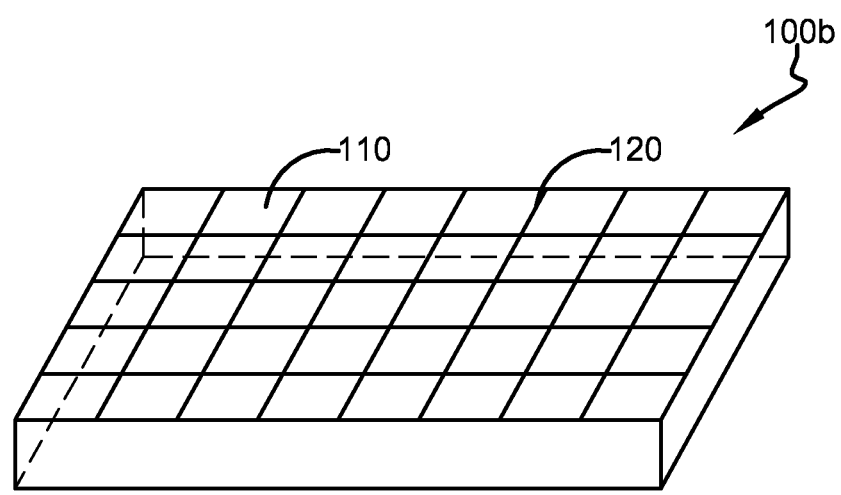
FIG. 1B is a perspective view of a slab scintillation crystal of an embodiment including pixelation grooves.
Figure 2A:
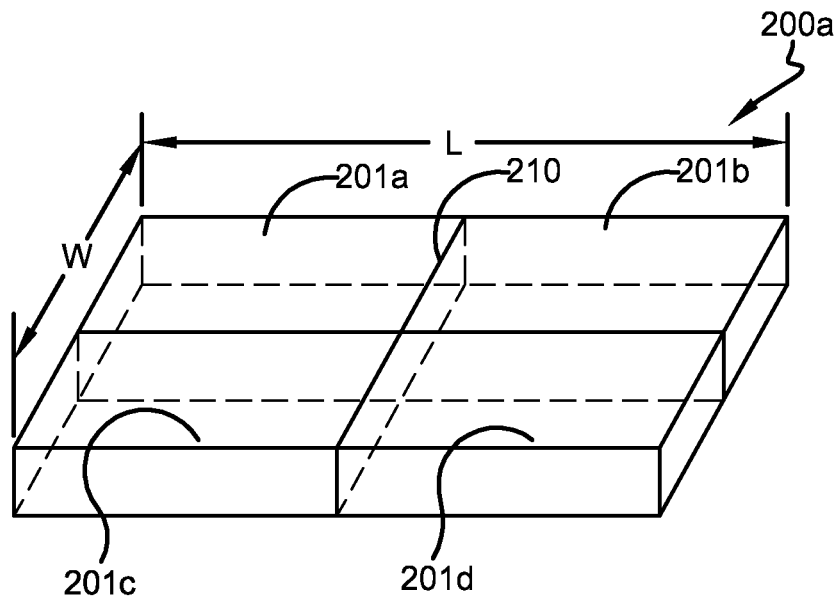
FIG. 2A is a perspective view of a plurality of joined scintillation crystals of an embodiment.
Figure 2B:
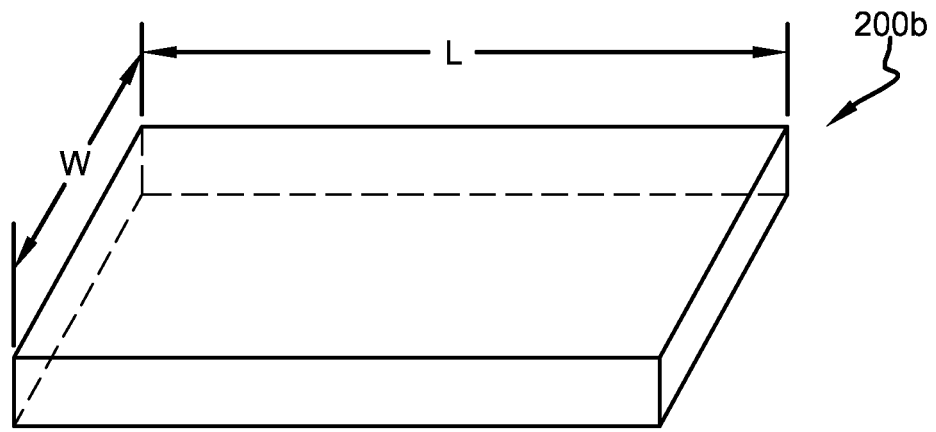
FIG. 2B is a perspective view of a slab scintillation crystal of an embodiment.
Figure 3:
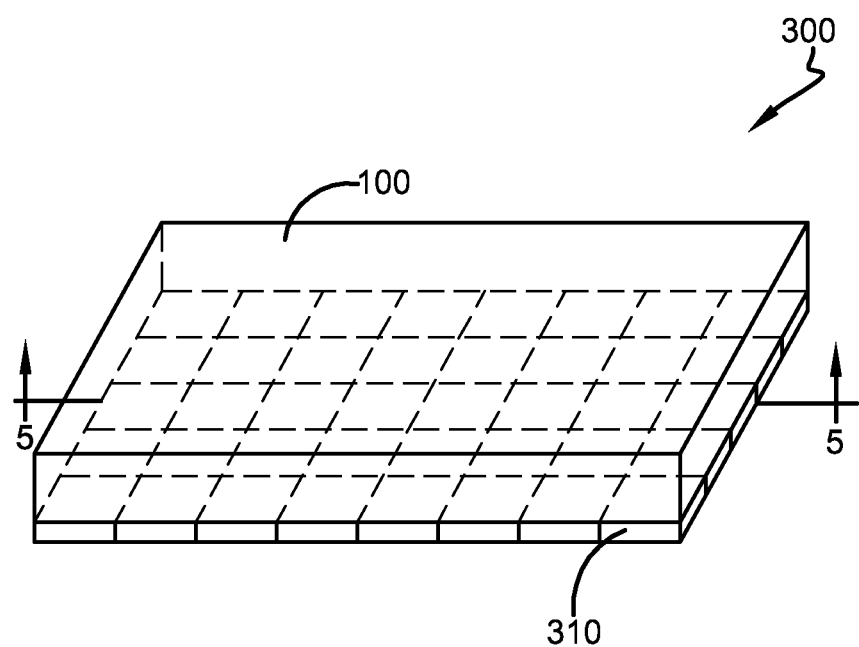
FIG. 3 is a perspective view of a PET/SPECT detector of an embodiment.
Figure 4:
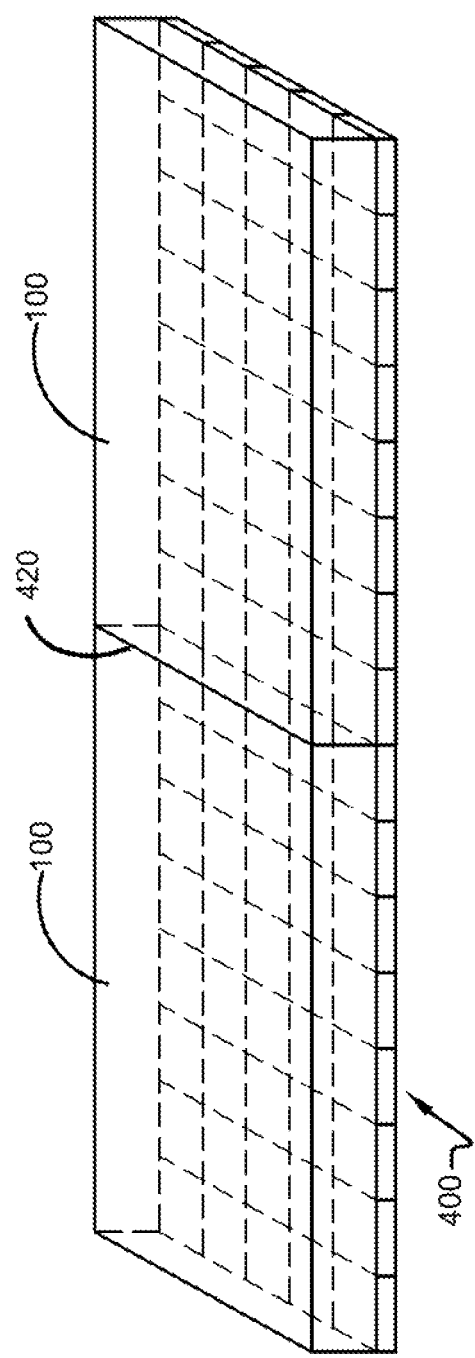
FIG. 4 is a perspective view of a pair of edge-abutting PET/SPECT detectors.

As shown in FIG. 3, according to some embodiments a scintillation detector 300 can comprise a single scintillation crystal 100, wherein a major surface of the crystal 100 is in optical communication with a plurality of photoconverters 310 arranged in a two dimensional array. Suitable photoconverters can include, without limitation, silicon photomultipliers and/or avalanche photodiodes. As discussed above, the single crystal 100 can alternatively comprise a plurality of joined crystals such as 200a of FIG. 2A and/or can include pixelation grooves such as that of 100b of FIG. 1B. FIG. 4 illustrates that detectors 300 of some embodiments can be juxtaposed with one another forming an edge-abutted pair 400 of detectors 300. In such embodiments, the scintillation crystal slabs 100, 100' are separated by an air interface 420.

Figure 5A:
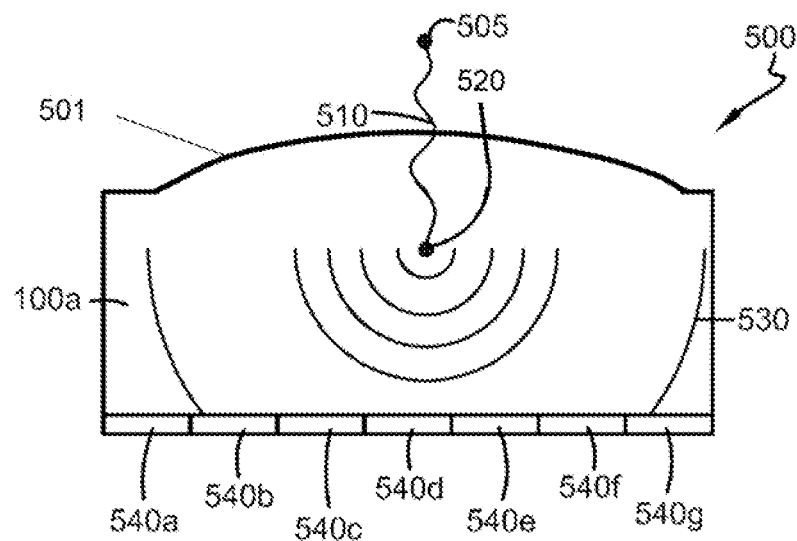
FIG. 5A is a cross sectional view of the detector of FIG. 3.
Figure 5B:
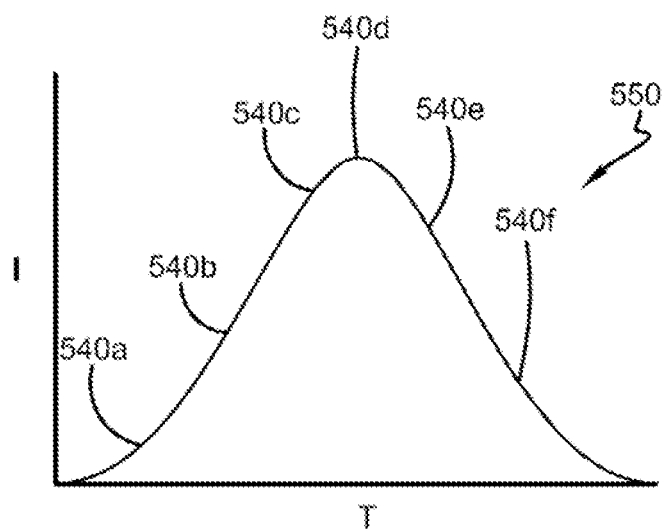
FIG. 5B is a graph of a signal resulting from wave front detection.

Turning to FIG. 5A, a cross sectional view of the detector of FIG. 3 is shown during detection of a scintillation event. According to some embodiments, a 511 keV gamma photon 505 resulting from $\beta^+$ decay enters the scintillation crystal 100a and travels 510 to a depth where it interacts with, i.e. is absorbed by, the scintillation crystal 100a. Subsequently, the scintillation crystal relaxes and emits a plurality of visible spectrum photons defining a scintillation event 520. The photon wave front 530 propagates through the scintillation crystal 100a and is characterized by a light pulse duration of about 10 to 100 nanoseconds, or as in the case of LYSO, about 40 nanoseconds. The wave front 530 reaches the photoconverters 540a-g, which are polled simultaneously to obtain a first digital sample measurement of the wave front 530. The photoconverters 540a-g are then simultaneously polled repeatedly to obtain a time series of digital samples 560a-f of the wave front 530 defining an electronic signal pulse 550. One of skill in the art will recognize that while only a one-dimensional array of photoconverters 540a-f is shown, the entire two-dimensional array is engaged in measurement of the wave front 530. Detection is discussed in terms of a one-dimensional array only to facilitate illustration.

Although the foregoing description is that of a single scintillation event, one of skill in the art will recognize that in actual operation a plurality of scintillation events can occur close enough in time so that either their wave fronts overlap, or the temporal resolution of the detector is exceeded, resulting in pulse pile-up and/or tail pile-up. Furthermore, pulse pile-up can result in contaminated data sets including, for instance, incorrect measurements of pulse energy. Accordingly, some embodiments further comprise methods for correcting, mitigating, and/or eliminating pulse pile-up. For example, some embodiments can include algorithms for deconvoluting overlapping pulses, detecting and rejecting overlapping pulses, or other suitable correction methods.

According to some embodiments, one or more cross correlation, interpolation, and/or super resolution algorithms can be applied to the pulse data 550 to increase the temporal resolution by about fifty-fold resulting in a temporal resolution of up to about 4 ps. Such high temporal resolution enables the high precision calculation of parameters including, without limitation, x-y annihilation position, gamma photon time-of-flight (TOF), gamma photon depth of interaction (DOI), scintillation event position, pulse energy, and/or pulse time or any combination thereof. Particularly, some representative ranges of precision obtainable according to embodiments of the invention are included in Table 1.

TABLE 1

| Parameter | Precision |
| --- | --- |
| x-y annihilation position | up to +/− 1 or 2 mm |
| gamma photon TOF | up to +/− 40 ps |
| scintillation pulse time | up to +/− 40 ps |
| scintillation DOI | up to +/− 1 to 3 mm |
| Energy Resolution | up to +/− 2 to 10% |

The embodiments have been described, hereinabove and shown in the various drawing views, which are included for purposes of illustrating embodiments of the invention and not for limiting the same. Thus, it will be apparent to those skilled in the art that the above methods and apparatuses may incorporate changes and modifications without departing from the general scope of this invention. Accordingly, it is intended to include all such modifications and alterations insofar as they come within the scope of the appended claims or the equivalents thereof.

We claim:

1. A slab detector, comprising:
   a scintillation crystal slab having a first major surface for receiving gamma rays, the first major surface including a reflective coating suitable for reflecting scintillation photons, a second major surface being free from reflective coatings and spaced apart from the first major surface defining a thickness, wherein the first and second major surfaces are each bounded by four edges which collectively define four minor surfaces, each minor surface including a reflective coating suitable for reflecting scintillation photons, wherein the scintillation crystal slab is free from pixelation grooves; and
   a plurality of photoconverters each in optical communication with the second major surface of the scintillation crystal and defining a two dimensional array, wherein each photoconverter abuts adjacent photoconverters.

2. The detector of claim 1, wherein the scintillation crystal slab further comprises one or more pixelation grooves.

3. The detector of claim 1, wherein one of the first or second major surfaces is curved, defining a lens.

4. The detector of claim 3, wherein the lens is adapted to focus scintillation photons on a predetermined portion of the two-dimensional array of photoconverters, or the lens is adapted to collimate scintillation photons such that they impinge the two-dimensional array of photoconverters at a perpendicular angle relative to the two-dimensional array.

5. The detector of claim 1, wherein the scintillation crystal comprises a material selected from one or more of cerium doped lutetium yttrium orthosilicate, sodium doped cesium iodide, bismuth germinate, cerium doped gadolinium orthosilicate, thallium doped sodium iodide, barium fluoride, cerium doped yttrium aluminate, cerium doped lutetium oxyorthosilicate, lanthanum bromide, cerium doped lanthanum bromide, or any combination thereof.

6. The detector of claim 1, wherein the plurality of photoconverters is selected from one or more of a silicon photomultiplier, or an avalanche photodiode.

7. The detector of claim 1, further comprising a data processing module in electronic communication with each of the photoconverters, and adapted to collect data from each photoconverter simultaneously and in a manner suitable for decimation in time sampling of a photon wave front in real time.

8. The detector of claim 1, wherein a plurality of detectors according to claim 1 are adapted to be juxtaposed with each other such that the scintillation crystal slabs of the respective detectors abut edgewise.

9. The detector of claim 1, wherein the scintillation crystal slab comprises a single crystal.

10. The detector of claim 1, where the scintillation crystal slab comprises a plurality of crystals joined by an index-matching material.

11. A slab detector, comprising:
    a scintillation crystal slab having a first major surface for receiving gamma rays, the first major surface including a reflective coating suitable for reflecting scintillation photons, a second major surface including a reflective coating suitable for reflecting scintillation photons and spaced apart from the first major surface defining a thickness, wherein the first and second major surfaces are each bounded by four edges which collectively define four minor surfaces, each minor surface being free from reflective coatings; and
    a plurality of photoconverters in optical communication with a minor surface of the scintillation crystal slab, and wherein each minor surface is in optical communication with at least one photoconverter.

12. The detector of claim 11, wherein the scintillation crystal slab comprises a single crystal.

13. The detector of claim 11, where the scintillation crystal slab comprises a plurality of crystals joined by an index-matching material.

14. The detector of claim 11, wherein one or more surfaces is curved, defining a lens.

15. The detector of claim 14, wherein the lens is adapted to focus scintillation photons on a predetermined portion of the plurality of photoconverters, or the lens is adapted to collimate scintillation photons such that they impinge the plurality of photoconverters at a perpendicular angle relative to the two-dimensional array.

16. The detector of claim 11, wherein the scintillation crystal comprises a material selected from one or more of cerium doped lutetium yttrium orthosilicate, sodium doped cesium iodide, bismuth germinate, cerium doped gadolinium orthosilicate, thallium doped sodium iodide, barium fluoride, cerium doped yttrium aluminate, cerium doped lutetium oxyorthosilicate, lanthanum bromide, cerium doped lanthanum bromide, or any combination thereof.

17. The detector of claim 11, wherein the plurality of photoconverters is selected from one or more of a silicon photomultiplier, or an avalanche photodiode.

18. The detector of claim 11, further comprising a data processing module in electronic communication with each of the photoconverters, and adapted to collect data from each photoconverter simultaneously and in a manner suitable for decimation in time sampling of a photon wave front in real time.

19. A slab detector, comprising:
    a scintillation crystal slab comprising a single crystal having a first major surface for receiving gamma rays, the first major surface including a reflective coating suitable for reflecting scintillation photons, a second major surface being free from reflective coatings and spaced apart from the first major surface defining a thickness, wherein the first and second major surfaces are each bounded by four edges which collectively define four minor surfaces, each minor surface including a reflective coating suitable for reflecting scintillation photons, and wherein one of the first or second major surfaces is curved, defining a lens; and
    a plurality of photoconverters each in optical communication with the second major surface of the scintillation crystal and defining a two dimensional array, wherein each photoconverter abuts adjacent photoconverters, wherein the lens is adapted to focus scintillation photons on a predetermined portion of the plurality of photoconverters, or the lens is adapted to collimate scintillation photons such that they impinge the two-dimensional array of photoconverters at a perpendicular angle relative to the two-dimensional array.

* * * * *